United States Patent
Ryu et al.

(10) Patent No.: US 9,456,608 B2
(45) Date of Patent: Oct. 4, 2016

(54) PLANT DISEASE RESISTANCE-INDUCING GENE FROM SOIL METAGENOME AND USES THEREOF

(71) Applicant: KOREA RESEARCH INSTITUTE OF BIOSCIENCE AND BIOTECHNOLOGY, Daejeon (KR)

(72) Inventors: Choong Min Ryu, Daejeon (KR); Hyo Bee Park, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 200 days.

(21) Appl. No.: 14/083,219

(22) Filed: Nov. 18, 2013

(65) Prior Publication Data

US 2014/0140960 A1   May 22, 2014

Related U.S. Application Data

(63) Continuation-in-part of application No. PCT/KR2012/003993, filed on May 21, 2012.

(30) Foreign Application Priority Data

May 20, 2011 (KR) .......................... 10-2011-0047649

(51) Int. Cl.
| | |
|---|---|
| *A01N 63/02* | (2006.01) |
| *C12N 15/70* | (2006.01) |
| *C12N 15/82* | (2006.01) |
| *C12N 15/52* | (2006.01) |

(52) U.S. Cl.
CPC .............. *A01N 63/02* (2013.01); *C12N 15/52* (2013.01); *C12N 15/70* (2013.01); *C12N 15/8279* (2013.01); *C12N 15/8281* (2013.01)

(58) Field of Classification Search
None
See application file for complete search history.

(56) References Cited

FOREIGN PATENT DOCUMENTS

| KR | 10-2006-0022338 A | 3/2006 |
| KR | 10-2009-0032676 A | 4/2009 |
| KR | 10-2010-0091749 A | 8/2010 |
| KR | 10-0952754 B1 | 8/2010 |
| KR | 10-0986161 B1 | 10/2010 |
| WO | WO2008-100112 A1 | 6/2002 |

OTHER PUBLICATIONS van Elsas et al, Trends in Biotechnology (2008) 26: 591-601.*
Zimaro et al, Journal of Biomedicine and Biotechnology vol. 2011, Article ID 354801 pp. 1-12.*
International Search Report for PCT/KR2012/003993.
Amann et al., "Phylogenetic Identification and In Situ Detection of Individual Microbial Cells without Cultivation," Microbiological Reviews, Mar. 1995, p. 143-169, vol. 59, No. 1.
Torsvik et al., "Determination of Bacterial DNA in Soil," Soil Biol. Biochem. vol. 10, pp. 7 to 12, 1978.
Handelsman et al., "Molecular biological access to the chemistry of unknown soil microbes: a new frontier for natural product," Chemistry & Biology, vol. 5, No. 10, R245-249 (1998).
Schmidt et al., Analysis of a marine picoplankton community by 16S rRNA gene cloning and sequencing, J. Bacteriol. 1991, 173(14): 4371-4378.
Morris et al., "SAR11 clade dominates ocean surface bacterioplankton communities," Nature, 2002, vol. 420: 806-810.

* cited by examiner

*Primary Examiner* — Ashley K Buran
(74) *Attorney, Agent, or Firm* — The PL Law Group, PLLC

(57) ABSTRACT

The present invention relates to a recombinant vector containing a plant disease resistance-related 1B8-4-D7 gene from the soil metagenome, a host cell transformed with the recombinant vector, a recombinant protein produced by the transformed host cell, a plant disease resistance enhancer including the transformed host cell or the recombinant protein as an effective component, a method of enhancing resistance against plant pathogens including eliciting induced resistance by treating a plant with a composition including the transformed host cell or the recombinant protein, and a preparation for controlling plant disease including the transformed host cell or the recombinant protein.

9 Claims, 9 Drawing Sheets

FIG. 1

| Source | vector | size (kb) | Total clone | Total metagenome size (Kb) | (Mb) | No. of Vial | No. of clones | ID |
|---|---|---|---|---|---|---|---|---|
| Seongnyugul cave | fosmid | 35 | 2,000 | 70000 | 70 | 10 | 2,000 | G1-13 |
| | fosmid | 35 | 8,185 | 286475 | 286.5 | 21 | 8,185 | |
| China salt lake | fosmid | 35 | 1,215 | 42525 | 42.5 | 5 | 1,215 | G46-50 |
| | fosmid | 35 | 5,850 | 204750 | 204.8 | 25 | 5,850 | |
| Forest topsoil and pine rhizosphere soil in Yuseong, Daejeon | fosmid | 35 | 243 | 8505 | 8.5 | 25 | 243 | G77-101 |
| Forest top soil in Gwangneung arboretum, Gyeonggido | fosmid | 35 | 239 | 8365 | 8.4 | 10 | 239 | G104-113 |
| Forest top soil in Gwangneung arboretum, Gyeonggido-II | fosmid | 35 | 239 | 8365 | 8.4 | 15 | 239 | G114-128 |
| Crop field soil in Guysan, | fosmid | 35 | 192 | 6720 | 6.7 | 19 | 192 | G2377-2396, G2383-4 |
| Crop field soil in Eumseonggun, Chungcheongbukdo | fosmid | 35 | 255 | 8925 | 8.9 | 14 | 255 | G2397-96, G2402, G2409-2413, G2353, 2420, 2423, 2425-26, 2428, 2430, 2432, 2438 |
| Field soil in Cheongsonggun, Gyeongsangbukdo | fosmid | 35 | 233 | 8155 | 8.2 | 16 | 233 | G2437, G2439, G2441, G2443, G2445, G2447, G2449-50, G2452, G2455, G2456, G2458, G2460, G2463, G2464-65 |
| Tidal flat in Janghwa-ri, Ganghwa | fosmid | 31 | 284 | 9940 | 9.9 | 25 | 284 | G2414-7, G2419, G2421-22, G2424, G2427, G2429, G2431, G2433, G2434-36, G2438, G2440, G2442, G2444, G2446, G2448, G2451, G2453-54, G2457, G2459, G2461, G2381, G2383 |
| Rhizosphere soil (suppressive soil) in Yeongyanggun, Gyeongsangbukdo | fosmid | 35 | 182 | 6370 | 6.4 | 7 | 182 | G2467-2480 |
| | | | | 6370 | 6.4 | 7 | | |
| Yongdu-beach seawater in Daecheon, Chungcheonbukdo | fosmid | 35 | 12,500 | 437500 | 437.5 | 5 | 12,500 | G7689-7693 |
| Chungcheongnamdo Seohaean salt pond | fosmid | 35 | 2,244 | 78540 | 78.5 | 7 | 2,244 | G7754-7800 |
| The Saemangeum reclaimed land mud flat in Jeollabuk-do buan | fosmid | 35 | 386,400 | 13524000 | 13524 | 25 | 386,400 | G7803-7968 |
| Paddy soil and rice rhizosphere in Asan and Gongju, Chungcheongnamdo and Suncheon, Jeollanamdo | fosmid | 35 | 80,000 | 2800000 | 2800 | 25 | 80,000 | G8169-8218 |
| Grassland forest topsoil in Jindongyegok, Injesi, Jeomboongsan, Gwangwondo | fosmid | 35 | 49,700 | 1739500 | 1739.5 | 25 | 49,700 | G8256-8305 |
| The shore sediment in the north pole base | fosmid | 35 | 60,000 | 2100000 | 2100 | 2 | 60,000 | G8312-8335 |
| The shore sediment in the north pole base | fosmid | 35 | 60,000 | 2100000 | 2100 | 27 | 60,000 | G8312-8335 |
| Rhizosphere soil in Daejeodong, Gamcogu, Busan | pEPI-FOS5 | 38 | 64,000 | 2240000 | 2240 | 25 | 64,000 | G8358-8377 |
| Bloom water | pBACe3.6 | 8 | 2,000 | 70000 | 70 | 20 | 2,000 | G358-377 |
| reservoir water in Chungju lake, Chungiu, Chungcheolbukdo | pBACe3.6 | 14 | 1,000 | 35000 | 35 | 10 | 1,000 | G2495-96, G2503, G2506, G2553-5, G2558, G2560, G2571 |
| reservoir water in Dumpo lake, Asan, Chungcheolnamdo | pBACe3.6 | 15 | 1,000 | 35000 | 35 | 10 | 1,000 | G2581, G2586, G2589, G2598, G2599, G2603, G2609-3, G2613 |
| Cheongju-si Daecheong lake reservoir water | pBACe3.6 | 13 | 1,000 | 35000 | 35 | 9 | 1,000 | G2615, G2618, G2619, G2621, G2624, G2626, G2629, G2640, G2643 |
| reservoir water in Daecheong lake, Cheongju-si | pBACe3.6 | 13 | 1,000 | 35000 | 35 | 1 | 1,000 | G2646 |
| livestock shed flat soil in Paltan-myeon, Maegok, Hwaseong, Gyeonggido | pCC1BAC | 35 | 6,000 | 210000 | 35 | 25 | 6,000 | G7694-7753 |
| Bovine rumen | pCC1BAC | 35 | 5,232 | 183120 | 210 | 25 | 5,232 | G337-357 G3525-3636 |
| Shihwa lake soil | pCC1BAC | 35 | 4,900 | 140000 | 183.1 | 25 | 4,900 | G7754-7793 |
| The pine rhizosphere soil in Gwanaksan, Seoul | pCC1BAC | 35 | 10,000 | 350000 | 140 | 26 | 10,000 | G7989-7988 |
| | pCC1BAC | 35 | 10,000 | 350000 | 350 | 5 | 10,000 | G7989-7993 |
| | pBluelysis | 35 | 10,000 | 350000 | 350 | 25 | 10,000 | G8069-8093 |
| River soil in Gunsan, Chungcheolnamdo | pUC19 | 4 | 3,400 | 119000 | 119 | 25 | 3,400 | G3491-3524 |

SEQUENCE LISTING

<160> NUMBER OF SEQ ID NOS: 14

<210> SEQ ID NO 1
<211> LENGTH: 4342
<212> TYPE: DNA
<213> ORGANISM: soil metagenome

<400> SEQUENCE: 1

```
acgccaacaa aatccaactt accaatcaat agtacgtttt tggtatttca tatcaaagaa     60
agtttccatt actgaacttt caaaaaatat ttccatttcg tatttgataa gttacttatc    120
cgtacgggat aataattatg ctccgttaga agacatcgta gatgatttag catttacaga    180
tatgtcatcc atagatttga cggaattaag gaaaatgcag ttatcagcaa atgcgataag    240
tggtgctaac aaattgattg aacaaatcaa tagctatact acccgttcag cgagaaagga    300
aatgttccaa gcgttggata taatgttctc atttgacaaa gttgctacta ttgataggat    360
ttgtccacaa caaaaatatc ctgatgccaa caaacgtctg aaagacattc ttaccttgta    420
ttatggctat ttctctttta gcagtctgct ctatgatgat tctattttca atataaaaaa    480
ttataaaata caagaactta tgaaccagcc ccttcaacaa atatattatg gtgcaccagg    540
cactggaaag tcctatgcaa caaaaaaagt agttgcagag tacccagaaa cagttcgtac    600
aacctttcat cctgatagcg actattcaac ttttgtcggt gcctacaaac ctacaacgac    660
taaagaagaa cgctatggat tgaacggctc aaataccgtt gctctcgttt accccgaggg    720
tgaaaagaaa ggaaagaata ttaaagatgg caagatagta tacaagcttt gttaaacaag    780
catttctgaa ggcatacata aaggcttgga aactggttta aggatagctg tgctaatggg    840
aaagaactgt taccacagtt tcttgtaata gaggaaataa accgaggaaa ctgtgctcag    900
atattcggtg atttgttcca gctacttgac cgcaaaaacg gtttctcaga ataccccatt    960
gaggcagatg aagacattca gaaagctctt ctcgaagagg atcctgaaga tggactaagt   1020
tttagcaagg atggactgaa ttttacagct gagcagatta catatataaa ccagcaatat   1080
gacattgttg gtcagccaag tcaaaaagta gcagagaaaa tcagatatgg tcaagtatta   1140
gtactacctc ccaattttta tatctgggcc actatgaaca caagcgacca gagtctgttc   1200
ccgatagatt ctgccttcaa gcgccgttgg gagtggaagt tcatgaagat caagaagggg   1260
aaagacgaga acggcaacga gctggattgg aggattgttg tgaaagacaa agacgagaac   1320
atcgtcaaga ttaacgataa ggaatcgctc tcttggtggg acttcatcag caagattaac   1380
gaaatcatcg catcaatgac ctccagtgcc gacaaacagt tgggatattt cttctgcaag   1440
gctgacaacg aaggcgtaat cagcgcagaa actatcgtaa gtaaagtcat tttctacctt   1500
tggaacgacg tgttcaagga ctatggcttt gaggatgcct cactgttccc aatacaaaac   1560
gatagaagaa ggtaaggagg taatgaaaga cctcactttc cccgacttct tcgacgagga   1620
gggcgagaat gtgagcgaag tacgcctgaa aggtttcctt gaaagcgtaa taaactggaa   1680
aaaggaagaa cgaagagcag agctaatgta catcctgttt gaagaacatc agtatgaaag   1740
ccaccttgtg gagaaagttc tgaaggatat atatgtgctt caggatgtag acaagaaggt   1800
```

```
gagtgtacaa tatgtgggct atttctataa tccacacctg cgtgattgtg tgttcatctt    1860
acccaaggtg ctattgacag aacaagagac attagtgggt gtgaagcaga agtctggcga    1920
gcctgtgaca ccagaaatgg tgttagatcc gcagggtcag gtaaaactaa gcaaagagta    1980
cagaaagttc atatacgaat tctctgtgtg gatatacaga accttgaatg tattttacaa    2040
ggctaatccc aagagtaaag ctattctcta caagcacctg ccacaagctg caaagggca     2100
cagacatcag gcgaagacgt atctggatat cgtgctatcc ctcatcacct tcaatcaaga    2160
aaatcgcgat ttcgtactct tcactatcaa aaatctgcat agagggaaca acaaaattaa    2220
ctggtcgcgt actatctctc attcgcaggc ttttgtacag gataaggatg tagtttatct    2280
aaatccggtg aacaaaaaac gcattgtgaa ctatgaagag gaattgttcg tcatattcta    2340
tagcatccta aactatttga acggagctta tggtttccgt acgcccatca acatccaata    2400
cgaactgatt tgtggaaagc agtttaagca atatatgcag ggaatgggca agacgaggct    2460
gatgaaaata aggtacaaat acttctcgga caaagcattg caattgtggg acttgtgctt    2520
tgcattcttt gagaactctt atcggattgc catcaatact aatgcacagg agtatcttct    2580
ggccaagagc tttaatgttg tttttgaggc gatgatagat gaactgatag gcacacccca    2640
tcatgacatt cctaaaggac tggccgatca agacgatgga aagcgggtgg accatatgta    2700
cacagattta gcgttaacat ctgcagaagc ccaaacgaac agggaggtct attatattgg    2760
tgatagtaag tattataaga gtgggcatcc gttgacatcg gaatctatat ataagcaata    2820
cacgtatgcg cggaatgtca tacaatggaa tgtgaacctg tttgcgtcgg acgattctca    2880
atttgatgaa gacgagaaga agaatagaaa agaagacaag aaacgcttca gtaaaattca    2940
tctgcaagac aactcactta cagaaggtta tgatgtgatt cccaacttct ttatcagtgc    3000
ctttgttaat aatgacctca gtacaacgt  acaggagaac atacgaccac acaaagataa    3060
gaacaaggag cattgcacaa aggtttctta tcagttttct gaccgcttgt ttgacaggga    3120
tacgttgttt ctttcgcaat atgatgtgaa tttcctgtat gtactcttcc tatatgctcg    3180
caataaggcc aacgaaaaat ctcaatggaa agaacatgtt cggaagaaat tccgcgacga    3240
gataagggct gtcatccaga aagaattcat gatttatgct atgcgggcca gattgggagt    3300
tgatggtgca ttataccctgc aacagcattt ctacgaccta aatggcagag tgttccagcc    3360
atatggtgaa gaacgaatga cttatttcgc atatgctcgc tctactaaga atttggagaa    3420
aacccaagcg caatatgatg aattgtcacg atactttatt atcgagaaat gtggtatggg    3480
acaagacccc gcaggtagtg ctgaatcctg caattgaaca agaacttcag caacctgttg    3540
tacaatcgca atggctgaca ctacactatc tagaacgata tactggcaaa ggcattttag    3600
taggttatta caaggacgaa gctcatttga aatggattct tggacataat gataagggat    3660
cattggtata taacgtacgt ttgcaagtaa aaggtgagga gccaagagct ggtgcacata    3720
cagcgggctt ctatagtaaa aagaatatcc aattcattgt cctttatact gatggtgtag    3780
accaaacagg cgggtatcgt gtattccatg tgaaagacac ggccagcaaa gttacagaag    3840
aaagaatgcg tggaacgtgg tatccatttg acgtaaaagg accacatttc ttcttccgtt    3900
tcgatgagga agtaacaatt ggaaagttaa atattcgtga acttttggcg catctgcgag    3960
tgaaacacct tgaggagttc ggaactctcg aagagggtga gccaatgttt acaacagcag    4020
aggaagtatt gaagtttcga gattaaatgg ataaactctc tgcacaacaa cgctataaaa    4080
taattaaaac tatatagata tgagtctaag aatattcaag ttagaagagt atgatcatac    4140
```

-continued

```
tcatgagcgc gaacagttta gaaaattgtg ttcaattttg aaggatttgt atgacaagtc    4200
ggctgaaatg cacctgctgt ttgccaacat caacttcaac ggtgtgccac ttgacgcttt    4260
gctcataaaa cccgatgcaa ttactgtatt ggagtttaag aactatagtg gtaatgtgat    4320
tgcagcagaa aacggagatt gg                                              4342

<210> SEQ ID NO 2
<211> LENGTH: 664
<212> TYPE: PRT
<213> ORGANISM: soil metagenome

<400> SEQUENCE: 2

Met Ala Leu Arg Met Pro His Cys Ser Gln Tyr Lys Thr Ile Glu Glu
1               5                   10                  15

Gly Lys Glu Val Met Lys Asp Leu Thr Phe Pro Asp Phe Phe Asp Glu
            20                  25                  30

Glu Gly Glu Asn Val Ser Glu Val Arg Leu Lys Gly Phe Leu Glu Ser
        35                  40                  45

Val Ile Asn Trp Lys Lys Glu Arg Arg Ala Glu Leu Met Tyr Ile
    50                  55                  60

Leu Phe Glu Glu His Gln Tyr Glu Ser His Leu Val Glu Lys Val Leu
65                  70                  75                  80

Lys Asp Ile Tyr Val Leu Gln Asp Val Asp Lys Lys Val Ser Val Gln
                85                  90                  95

Tyr Val Gly Tyr Phe Tyr Asn Pro His Leu Arg Asp Cys Val Phe Ile
            100                 105                 110

Leu Pro Lys Val Leu Leu Thr Glu Gln Glu Thr Leu Val Gly Val Lys
        115                 120                 125

Gln Lys Ser Gly Glu Pro Val Thr Pro Glu Met Val Leu Asp Pro Gln
    130                 135                 140

Gly Gln Val Lys Leu Ser Lys Glu Tyr Arg Lys Phe Ile Tyr Glu Phe
145                 150                 155                 160

Ser Val Trp Ile Tyr Arg Thr Leu Asn Val Phe Tyr Lys Ala Asn Pro
                165                 170                 175

Lys Ser Lys Ala Ile Leu Tyr Lys His Leu Pro Gln Ala Gly Lys Gly
            180                 185                 190

His Arg His Gln Ala Lys Thr Tyr Leu Asp Ile Val Leu Ser Leu Ile
        195                 200                 205

Thr Phe Asn Gln Glu Asn Arg Asp Phe Val Leu Phe Thr Ile Lys Asn
    210                 215                 220

Leu His Arg Gly Asn Asn Lys Ile Asn Trp Ser Arg Thr Ile Ser His
225                 230                 235                 240

Ser Gln Ala Phe Val Gln Asp Lys Asp Val Val Tyr Leu Asn Pro Val
                245                 250                 255

Asn Lys Lys Arg Ile Val Asn Tyr Glu Glu Glu Leu Phe Val Ile Phe
            260                 265                 270

Tyr Ser Ile Leu Asn Tyr Leu Asn Gly Ala Tyr Gly Phe Arg Thr Pro
        275                 280                 285

Ile Asn Ile Gln Tyr Glu Leu Ile Cys Gly Lys Gln Phe Lys Gln Tyr
    290                 295                 300

Met Gln Gly Met Gly Lys Thr Arg Leu Met Lys Ile Arg Tyr Lys Tyr
305                 310                 315                 320

Phe Ser Asp Lys Ala Leu Gln Leu Trp Asp Leu Cys Phe Ala Phe Phe
                325                 330                 335
```

```
Glu Asn Ser Tyr Arg Ile Ala Ile Asn Thr Asn Ala Gln Glu Tyr Leu
                340                 345                 350

Leu Ala Lys Ser Phe Asn Val Val Phe Glu Ala Met Ile Asp Glu Leu
            355                 360                 365

Ile Gly Thr Pro His His Asp Ile Pro Lys Gly Leu Ala Asp Gln Asp
        370                 375                 380

Asp Gly Lys Arg Val Asp His Met Tyr Thr Asp Leu Ala Leu Thr Ser
385                 390                 395                 400

Ala Glu Ala Gln Thr Asn Arg Glu Val Tyr Tyr Ile Gly Asp Ser Lys
                405                 410                 415

Tyr Tyr Lys Ser Gly His Pro Leu Thr Ser Glu Ser Ile Tyr Lys Gln
            420                 425                 430

Tyr Thr Tyr Ala Arg Asn Val Ile Gln Trp Asn Val Asn Leu Phe Ala
        435                 440                 445

Ser Asp Asp Ser Gln Phe Asp Glu Asp Glu Lys Lys Asn Arg Lys Glu
450                 455                 460

Asp Lys Lys Arg Phe Ser Lys Ile His Leu Gln Asp Asn Ser Leu Thr
465                 470                 475                 480

Glu Gly Tyr Asp Val Ile Pro Asn Phe Phe Ile Ser Ala Phe Val Asn
                485                 490                 495

Asn Asp Leu Lys Tyr Asn Val Gln Glu Asn Ile Arg Pro His Lys Asp
            500                 505                 510

Lys Asn Lys Glu His Cys Thr Lys Val Ser Tyr Gln Phe Ser Asp Arg
        515                 520                 525

Leu Phe Asp Arg Asp Thr Leu Phe Leu Ser Gln Tyr Asp Val Asn Phe
530                 535                 540

Leu Tyr Val Leu Phe Leu Tyr Ala Arg Asn Lys Ala Asn Glu Lys Ser
545                 550                 555                 560

Gln Trp Lys Glu His Val Arg Lys Phe Arg Asp Glu Ile Arg Ala
                565                 570                 575

Val Ile Gln Lys Glu Phe Met Ile Tyr Ala Met Arg Ala Arg Leu Gly
                580                 585                 590

Val Asp Gly Ala Leu Tyr Leu Gln Gln His Phe Tyr Asp Leu Asn Gly
            595                 600                 605

Arg Val Phe Gln Pro Tyr Gly Glu Arg Met Thr Tyr Phe Ala Tyr
        610                 615                 620

Ala Arg Ser Thr Lys Asn Leu Glu Lys Thr Gln Ala Gln Tyr Asp Glu
625                 630                 635                 640

Leu Ser Arg Tyr Phe Ile Ile Glu Lys Cys Gly Met Gly Gln Asp Pro
                645                 650                 655

Ala Gly Ser Ala Glu Ser Cys Asn
            660

<210> SEQ ID NO 3
<211> LENGTH: 18
<212> TYPE: DNA
<213> ORGANISM: Artificial Sequence
<220> FEATURE:
<223> OTHER INFORMATION: Forward Primer for uantitative real time-
      polymerase chain reaction

<400> SEQUENCE: 3
aatatcccac tcttgccg                                                   18

<210> SEQ ID NO 4
<211> LENGTH: 18
```

```
<212> TYPE: DNA
<213> ORGANISM: Artificial Sequence
<220> FEATURE:
<223> OTHER INFORMATION: Reverse Primer for uantitative real time-
      polymerase chain reaction

<400> SEQUENCE: 4
cctggaggat catagttg                                              18

<210> SEQ ID NO 5
<211> LENGTH: 18
<212> TYPE: DNA
<213> ORGANISM: Artificial Sequence
<220> FEATURE:
<223> OTHER INFORMATION: Forward Primer for uantitative real time-
      polymerase chain reaction

<400> SEQUENCE: 5
atctcactct tctcatgc                                              18

<210> SEQ ID NO 6
<211> LENGTH: 18
<212> TYPE: DNA
<213> ORGANISM: Artificial Sequence
<220> FEATURE:
<223> OTHER INFORMATION: Reverse Primer for uantitative real time-
      polymerase chain reaction

<400> SEQUENCE: 6
tacctggagg atcatagt                                              18

<210> SEQ ID NO 7
<211> LENGTH: 18
<212> TYPE: DNA
<213> ORGANISM: Artificial Sequence
<220> FEATURE:
<223> OTHER INFORMATION: Forward Primer for uantitative real time-
      polymerase chain reaction

<400> SEQUENCE: 7
cttgtctcta cgcttctc                                              18

<210> SEQ ID NO 8
<211> LENGTH: 18
<212> TYPE: DNA
<213> ORGANISM: Artificial Sequence
<220> FEATURE:
<223> OTHER INFORMATION: Reverse Primer for uantitative real time-
      polymerase chain reaction

<400> SEQUENCE: 8
aacacgaacc gagttacg                                              18

<210> SEQ ID NO 9
<211> LENGTH: 21
<212> TYPE: DNA
<213> ORGANISM: Artificial Sequence
<220> FEATURE:
<223> OTHER INFORMATION: Forward Primer for uantitative real time-
      polymerase chain reaction

<400> SEQUENCE: 9
ttcacaacca ggcacgagga g                                          21

<210> SEQ ID NO 10
<211> LENGTH: 29
<212> TYPE: DNA
```

```
<213> ORGANISM: Artificial Sequence
<220> FEATURE:
<223> OTHER INFORMATION: Reverse Primer for uantitative real time-
      polymerase chain reaction

<400> SEQUENCE: 10
ccagacaagt caccgctacc ccaggctaa                                        29

<210> SEQ ID NO 11
<211> LENGTH: 21
<212> TYPE: DNA
<213> ORGANISM: Artificial Sequence
<220> FEATURE:
<223> OTHER INFORMATION: Forward Primer for uantitative real time-
      polymerase chain reaction

<400> SEQUENCE: 11
tcacccttat cttcgctgct c                                                21

<210> SEQ ID NO 12
<211> LENGTH: 20
<212> TYPE: DNA
<213> ORGANISM: Artificial Sequence
<220> FEATURE:
<223> OTHER INFORMATION: Reverse Primer for uantitative real time-
      polymerase chain reaction

<400> SEQUENCE: 12
gttgcatgat ccatgtttgg                                                  20

<210> SEQ ID NO 13
<211> LENGTH: 20
<212> TYPE: DNA
<213> ORGANISM: Artificial Sequence
<220> FEATURE:
<223> OTHER INFORMATION: Forward Primer for uantitative real time-
      polymerase chain reaction

<400> SEQUENCE: 13
tcagaagacc ccaaaagctc                                                  20

<210> SEQ ID NO 14
<211> LENGTH: 20
<212> TYPE: DNA
<213> ORGANISM: Artificial Sequence
<220> FEATURE:
<223> OTHER INFORMATION: Reverse Primer for uantitative real time-
      polymerase chain reaction

<400> SEQUENCE: 14
ttgatcaccg ctccgtgaag                                                  20
```

PLANT DISEASE RESISTANCE-INDUCING GENE FROM SOIL METAGENOME AND USES THEREOF

CROSS-REFERENCE TO RELATED APPLICATIONS

The present application is a continuation-in-part application to International Application No. PCT/KR2012/003993, with an International Filing Date of May 21, 2012, which claims the benefit of Korean Patent Application No. 10-2011-0047649, filed in the Korean Intellectual Property Office on May 20, 2011, the entire contents of which are incorporated herein by reference.

BACKGROUND

1. Field of the Invention

The present invention relates to a plant disease resistance-inducing gene from the soil metagenome and a use thereof. More specifically, it relates to a recombinant vector containing a plant disease resistance-inducing 1B8-4-D7 gene from the soil metagenome, a host cell transformed with the recombinant vector, a recombinant protein produced by the transformed host cell, a plant disease resistance enhancer including the transformed host cell or the recombinant protein as an effective component, a method of enhancing resistance against plant pathogens having elicited induced resistance by treating a plant with a composition including the transformed host cell or the recombinant protein, and a preparation for controlling plant disease having the transformed host cell or the recombinant protein.

2. Description of the Related Art

There is a difference between the numbers of various microorganisms observed from the natural environment and the numbers of colonies shown in a culture plate, and the difference can be defined as the 'plate-count anomaly.' (Amann et al. (1995) *Microbiol. Rev.* 59: 143-169). In the late 1970s, there was a suggestion that the DNA of microorganisms should be directly isolated from their natural habitat and the constitutive genes of their genome should be studied as they are (Torsvik V. L. and Goks J. (1978) *Soil Biology & Biochemistry* 10: 7-12), which later led to the new 'metagenome' terminology. Metagenome was defined as a "group of genome of all microorganisms that are present in a certain given environment" (Handelsman et al. (1998) *Chem. Biol.* 5: R245-249), and the study of the direct cloning of metagenomic DNA was first led by Pace and DeLong in the U.S. (Schmidt et al. (1991) *J. Bacteria* 173: 4371-4378).

Performing a study of microorganisms after completely identifying and classifying them via culture is one particular way to study the microorganisms. However, this method is difficult to realize in the real world. For example, although SAR11 bacteria are a dominant species in various sea environments all over the world, only recently has it been successfully cultured, but the culture thereof was not based on conventional pure culture methods, which involve growing a colony on a solid medium (Morris et al. (2002) *Nature* 420: 806-810). Further, with the simulation of a natural environment for culture growth using the diffusion chamber method, it became possible to obtain colonies of microorganisms which could not be cultured before because it was found that some microorganisms do not grow on artificial media, but can grow via natural interactions with other microorganisms.

The biggest advantages for studying microorganisms and their diversity via studying the metagenome are that, first, a gene can be studied without culture, and second, a comprehensive understanding can be made regarding the surrounding environment.

An enzyme is a complex protein catalyst produced by a living organism, and an enzyme can also referred to as a biocatalyst. The reason why the metagenome has received attention in recent years is that it can be useful, as its application area, for the search of new substances or enzymes. Examples of enzymes that are widely used in industrial processes include chitinase, lipase/esterase, protease, amylase, DNAse, and xylanase, which mainly hydrolyze polymeric material. Other enzymes include polyketide synthase, 4-hydroxybutyrate DH, and oxygenase (Lorenz et al. (2002) *Curr Opin Biotechnol* 13: 572-577). However, the recent tendency is, apart from the enzymes being used for hydrolyzing a polymer, to utilize enzymes originating from microorganisms or the metagenome as a catalyst in a reaction required for a chemical synthetic process.

A group of genes from the soil metagenome, which encode antibiotic resistance, have been disclosed in Korean Patent Registration No. 0952754, and a novel lipase gene from the soil metagenome and a lipase protein encoded by the lipase gene have been disclosed in Korean Patent Registration No. 0613694. However, there is absolutely no disclosure suggesting that a novel gene isolated from the soil metagenome can be used for enhancing the disease resistance of a plant as described in the present invention.

SUMMARY OF THE INVENTION

One embodiment of the present invention is devised in view of the circumstances and needs described above, and identifies gene(s) exhibiting induced systemic resistance against soft-rot disease in tobacco, bacterial canker caused by *Xanthomonas axonopodis* pv. *Vesicatoria* in peppers, or viral diseases caused by cucumber mosaic virus (CMV), via using a soil metagenome library.

One embodiment of the present invention provides a plant disease resistance-inducing 1B8-4-D7 gene from the soil metagenome.

In another embodiment, the present invention provides a recombinant vector containing the gene.

In yet another embodiment, the present invention provides a host cell transformed with the recombinant vector.

In still yet another embodiment, the present invention provides a recombinant protein produced by the transformed host cell.

In one embodiment, the present invention provides a plant disease resistance enhancer including the transformed host cell or the recombinant protein as an effective component.

In yet another embodiment, the present invention provides a method of enhancing resistance against plant pathogens including eliciting induced resistance via treating a plant with a composition including the transformed host cell or the recombinant protein.

In still yet another embodiment, the present invention provides a preparation for controlling plant disease including the transformed host cell or the recombinant protein.

A plant treated with the 1B8-4-D7 gene from the soil metagenome of the present invention is effective for controlling soft-rot disease in tobacco, bacterial canker in peppers, or viral diseases caused by CMV, and thus the invention will be useful for increasing plant productivity.

Furthermore, the composition of the present invention is environmentally friendly and has no human toxicity, therefore, is highly safe.

BRIEF DESCRIPTIONS OF DRAWINGS

FIG. 1 illustrates the metagenome pool supplied from Micro Bank.

Figure 4:
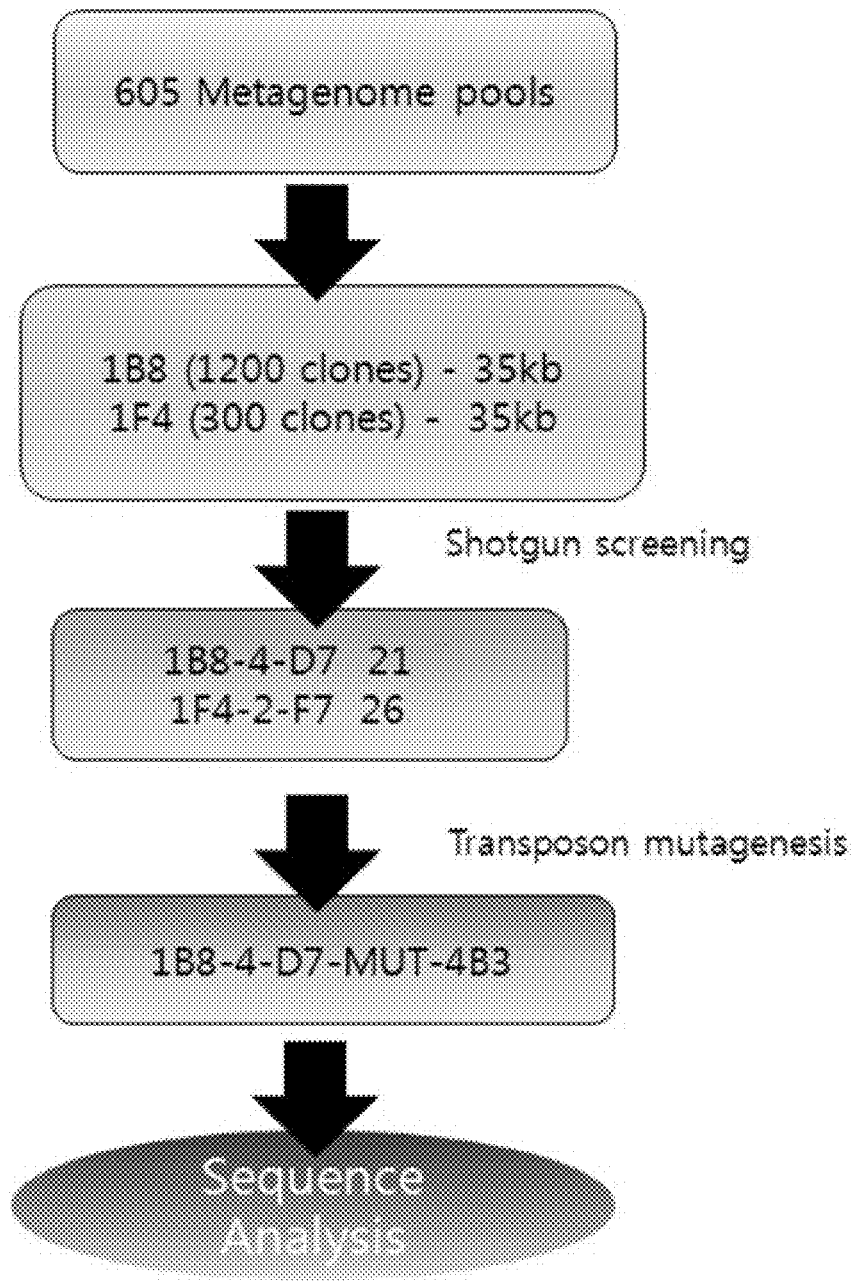

FIG. 4 illustrates a series of processes for obtaining a single clone from the soil metagenome library pool that included an average of 1000 clones (genes). The induced resistance determination was first made for 605 pools. The experiment for determining the induced resistance was performed after isolating a colony from the selected pool. After selecting two clones, the determination was made to see which region of the gene inserted into the plasmid exhibited the induced resistance.

Figure 5A:
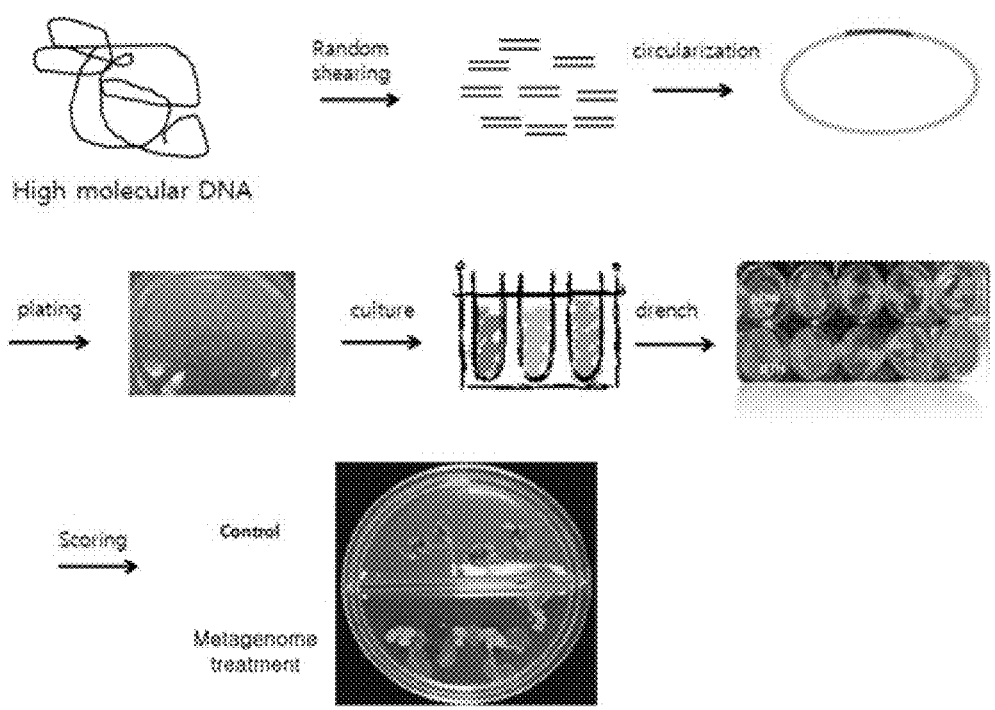
Figure 5B:
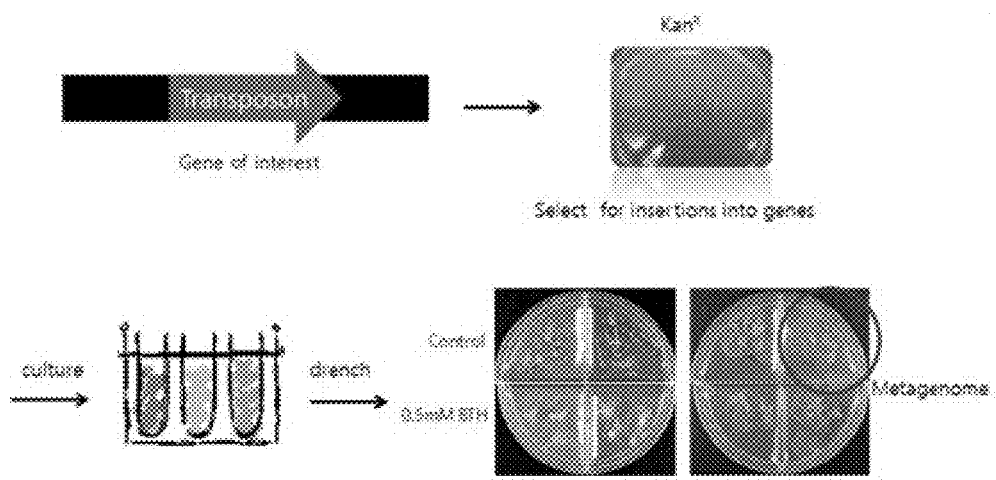

FIG. 5A illustrates the results of determining the induced resistance after the nucleotide sequence is randomly digested by using a shotgun method, inserted into a pUC118 vector, and expressed in *E. coli*, and FIG. 5B the results of the test for causing random mutagenesis of the selected clone by using a transposon mutagenesis method.

Figure 6A:
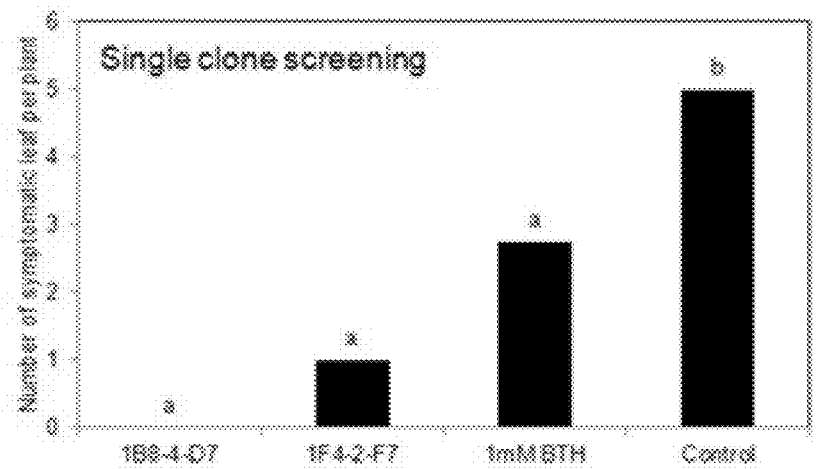
Figure 6B:
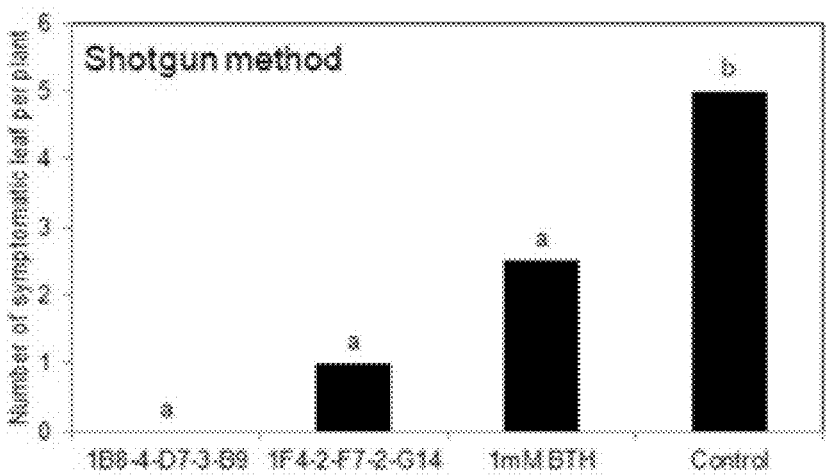
Figure 6C:
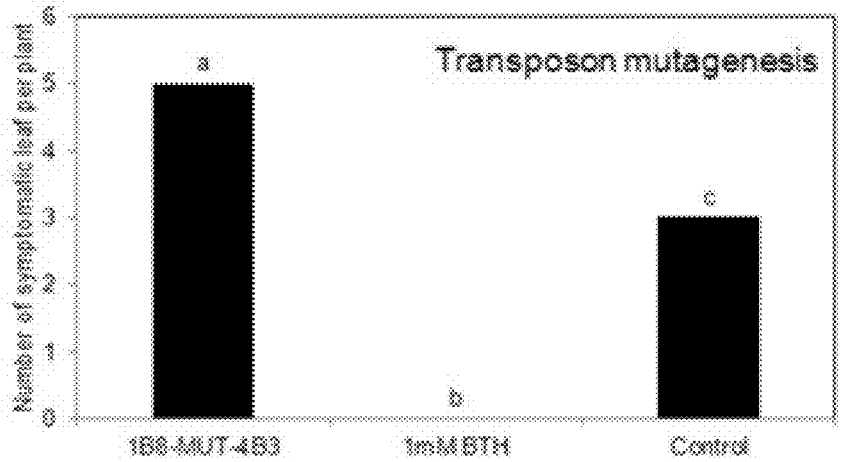

FIGS. 6A and 6B illustrate the results of observing symptoms of disease on Day 2 after inoculating the pathogen in order to examine the effect of the metagenome on in vitro expression of the induced resistance-inducing gene in tobacco. The positive control group and negative control group were treated with 1 mM BTH and sterilized distilled water, respectively. FIG. 6A shows the results of observing symptoms of disease in induced resistance, wherein the selected clones were examined as a subject. FIG. 6B shows the induced resistance test by using two monoclones. The induced resistance was shown in clones of 1B8-4-D7 and 1F4-2-F7 compared to the positive clone. FIG. 6C shows that a clone not exhibiting induced resistance shown in the shotgun process was selected from the clones obtained by the transposon mutagenesis method.

Figure 7A:
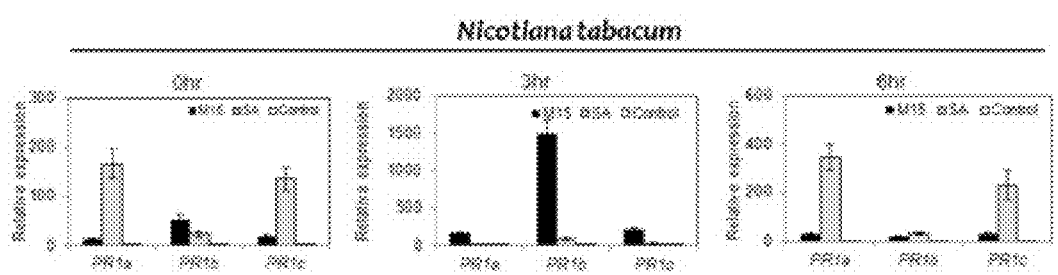
Figure 7B:
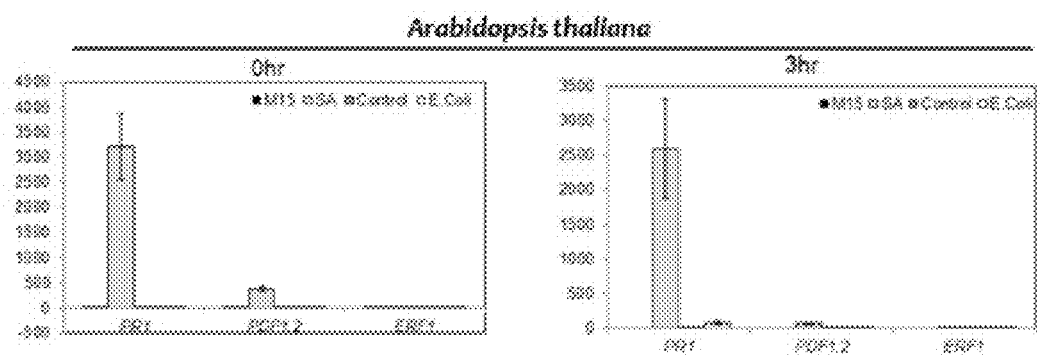

FIGS. 7A and 7B illustrate that the induced resistance is weaker in the M15 clone compared to the negative control group. FIG. 7A shows the results of qRT-PCR with extraction of tobacco RNA, 0 hours, 3 hours, or 6 hours after treating the tobacco leaves with pathogen. It was confirmed that, among the expressions of PR1a, PR1b, and PR1c (i.e., the resistance genes of tobacco), expression of PR1b at hour 3 was increased compared to the control group. FIG. 7B shows the expression of the resistance genes PR1, PDF1.2, and ERF in *Arabidopsis thaliana*. At both hour 0 and hour 3, the expression amount in the metagenome treatment group was lower than the positive control group, showing a similar pattern to the treatment group.

Figure 8A:
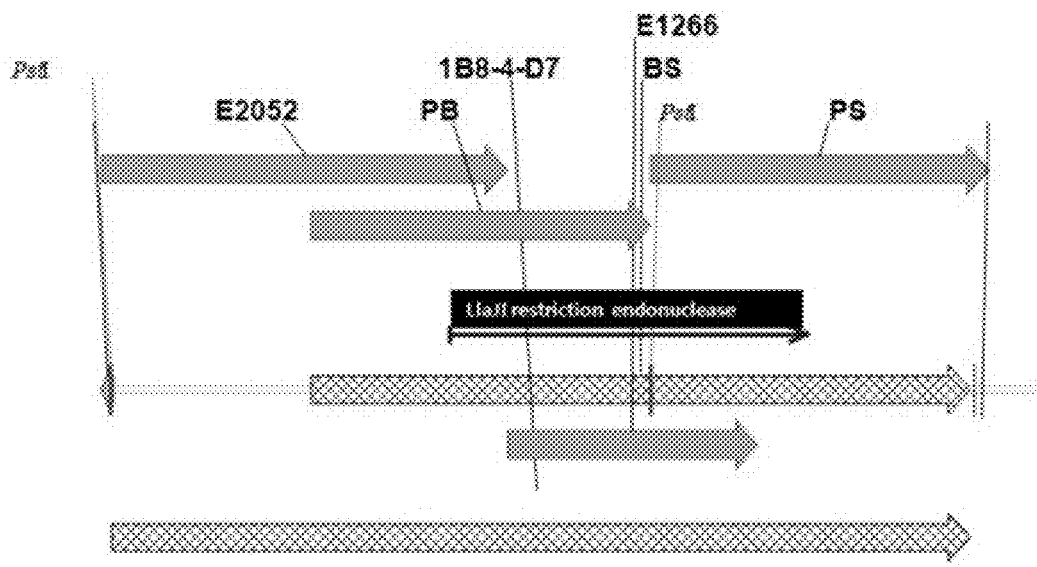
Figure 8B:
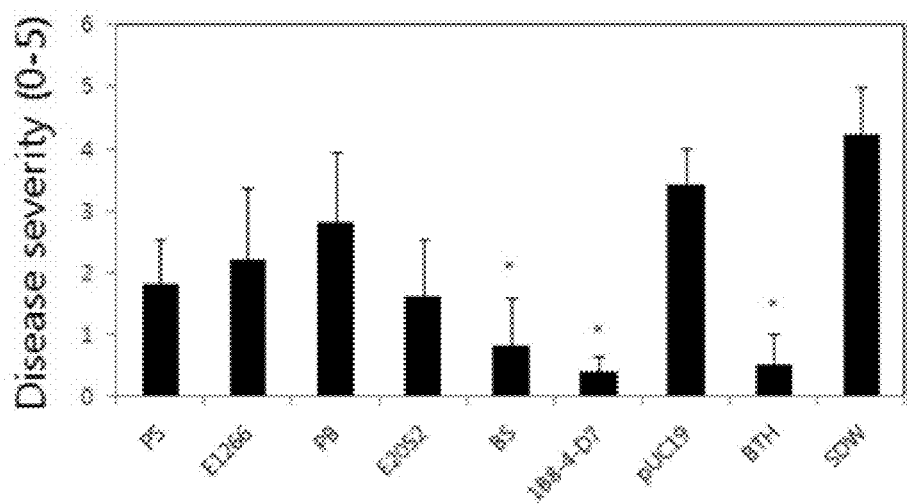

FIGS. 8A and 8B illustrate the results of induced resistance in selected metagenome clones against *Erwinia carotovora* subsp. *carotovora*, a casual pathogen of the soft-rot pathogen. FIG. 8A show the name and position of the clones of 1B8-4-D7 that are divided into 5 fragments around ORF. FIG. 8B show five fragments of the selected metagenome 1B8-4-D7 (i.e., PS, E1266, PB, E2052, and BS), vector control group pUC19, and water treatment (SDW) as a control group and treatment with BTH as a compound for inducing disease resistance. * represents the treatment group having significantly reduced disease occurrence compared to the control group pUC19 at P=0.05 levels based on ANOVA analysis. The disease severity is as follows: 0=no symptom of disease, 1=soft-rot symptom was observed from one leaf, 2=soft-rot symptom was observed from two leaves, 3=soft-rot symptom was observed from three leaves, 4=soft-rot symptom was observed from four leaves, and 5=soft-rot symptom was observed from the whole plant including the plant stalk.

Figure 9A:
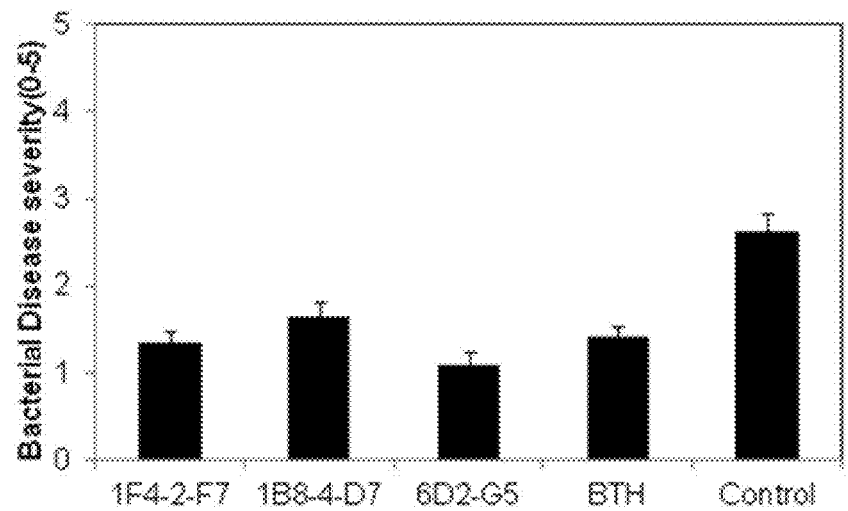
Figure 9B:
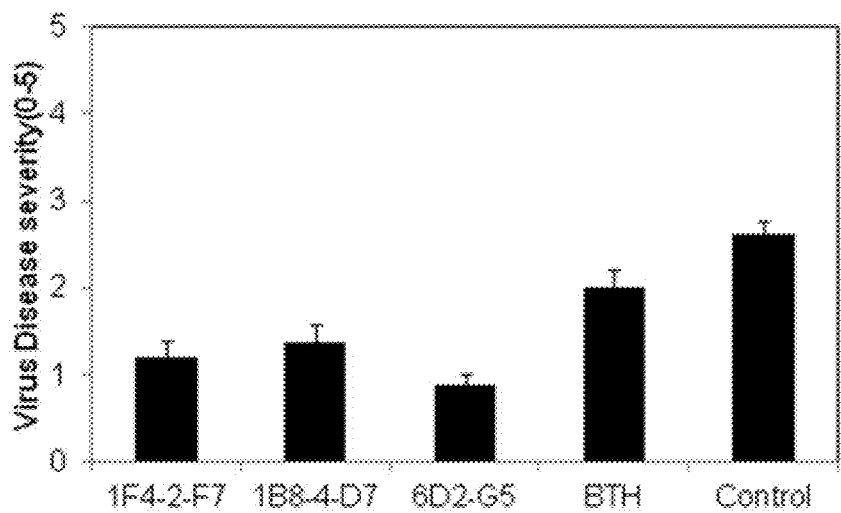

FIGS. 9A and 9B illustrate the results of induced resistance in the selected metagenome clones against pepper canker and viral disease. (A) Resistance to pepper canker. (B) Resistance to CMV.

DETAILED DESCRIPTION

In one embodiment of the present invention is the plant disease resistance-inducing 1B8-4-D7 gene from the soil metagenome. The gene of the present invention may consist of the nucleotide sequence represented by SEQ ID NO: 1 (i.e., 1B8-4-D7 gene), the nucleotide sequence from the $998^{th}$ to the $3,574^{th}$ nucleotide in SEQ ID NO: 1 (i.e., 6D2-G5 gene), or the nucleotide sequence from the $1,523^{rd}$ to the $3,517^{th}$ nucleotide in SEQ ID NO: 1 (i.e., restriction endonuclease coding gene). The protein encoded by the restriction endonuclease coding gene corresponds to the amino acid sequence of the SEQ ID NO: 2, and via causing induced systemic resistance in a plant, resistance to soft-rot disease in tobacco, bacterial canker in pepper, or a plant disease caused by CMV can be exhibited.

Further, homologs of the aforementioned nucleotide sequence are also included within the scope of the present invention. More specifically, the above described gene may include a nucleotide sequence which has at least 70%, at least 80%, at least 90%, and at least 95% homology with the nucleotide sequence of SEQ ID NO: 1. The "sequence homology percentage" for certain polynucleotides is identified by comparing comparative regions with two sequences that are optimally aligned. In this regard, a part of the polynucleotide in the comparative region may include additions or deletions (i.e., gaps) compared to the reference sequence (i.e., without any additions or deletions) relative to the optimized alignment of the two sequences.

In another embodiment, the present invention provides a recombinant vector including the gene of the present invention.

The term "vector" as used herein refers to DNA fragment(s) and nucleotide molecules that are delivered to a cell. Vectors can be used for the replication of DNA and may be independently reproduced in a host cell. The terms "delivery system" and "vector" are often interchangeably used. The term "expression vector" means a recombinant DNA molecule including a desired coding sequence and other appropriate nucleotide sequences that are essential for the expression of the operably-linked coding sequence in a specific host organism.

In another embodiment, the present invention also provides a host cell transformed with the aforementioned recombinant vector.

With respect to a host cell, any host cell known in the pertinent art with the ability to stably and continuously clone and express the vector of the present invention can be used.

Examples thereof include, without limitation, *Bacillus* sp. strain including *E. coli* JM109, *E. coli* BL21, *E. coli* RR1, *E. coli* LE392, *E. coli* B, *E. coli* X 1776, *E. coli* W3110, *Bacillus subtillus, Bacillus thuringiensis*, and the like, and intestinal bacterial strains including, without limitation, *Salmonella typhimurium, Serratia marcescens*, various *Pseudomonas* sp., and the like.

In addition, when a eukaryotic cell is transformed with the vector of the present invention, *Saccharomyces cerevisiae*, an insect cell, a human cell (e.g., CHO (Chinese hamster ovary), W138, BHK, COS-7, 293, HepG2, 3T3, RIN, and MDCK cell line), a plant cell, and the like can be used as a host cell.

In yet another embodiment, the present invention also provides a recombinant protein produced by the aforementioned transformed host cell. The recombinant protein is a recombinant protein that may be produced by *E. coli*, but as long as the produced recombinant protein can enhance the resistance to a plant disease, the host cell is without limitation. The recombinant protein may include, without limitation, the amino acid sequence of SEQ ID NO: 2.

In another embodiment, the present invention also provides a plant disease resistance enhancer including the aforementioned transformed host cell or the recombinant protein as an effective component. The plant disease resistance enhancer may contain, as an effective component, transformed *E. coli* or a recombinant protein that is produced by the transformed *E. coli*. However, as long as the transformed host cell or the recombinant protein produced by the transformed host cell can enhance the resistance to a plant disease, they are without limitation. The recombinant proteins may be the same as those described above.

In yet another embodiment, the present invention also provides a method of enhancing resistance against plant pathogens including eliciting induced resistance by treating a plant with a composition including the transformed host cell or the recombinant protein. The composition may contain, as an effective component, the aforementioned transformed host cell or recombinant protein. The composition may further include a stabilizer known in the pertinent art to stabilize a protein. The transformed host cell and recombinant protein may be the same as those described above. By causing induced systemic resistance in a plant, the composition may enhance resistance to various plant diseases, in addition to soft-rot disease in tobacco, bacterial canker in peppers, and disease caused by CMV.

In another embodiment, the present invention also provides a preparation for controlling plant disease including the transformed host cell or the recombinant protein. The transformed host cell and recombinant protein may be the same as those described above. By causing induced systemic resistance in a plant, the preparation for controlling plant disease can have an effect of controlling various plant diseases, in addition to soft-rot disease in tobacco, bacterial canker in peppers, and disease caused by CMV.

Herein below, the present invention is further explained via Examples. However, the following Examples are only intended to clearly illustrate the present invention without limitation of the scope of the present invention.

EXAMPLES

Materials and Methods

In Vitro Determination of Induced Systemic Resistance (ISR)

To determine ISR in 605 pools of the metagenome library, each library was cultured for 16 hours at 37° C. in an LB medium contained within a 96 well plate. Seven days after treating the plant roots with the same method as above, *Erwinia carotovora* subsp. *carotovora*, which is a pathogen causing soft-rot in tobacco plant, was inoculated and any symptoms of disease were monitored. The positive control group plant was treated with 1 mM BTH. The severity of disease (0 to 5), which is used as an indicator of ISR, was measured on Day 2 after inoculation with the pathogen (0: no symptoms of necrosis; 5: severe symptoms of necrosis).

Expression Analysis of the Resistance Gene

Expression of PR1a, PR1b, and PR1c related to disease resistance in tobacco was examined based on quantitative real time-polymerase chain reaction (qRT-PCR). Sequences of the primers that were used were as follows:

```
                                   (SEQ ID NO: 3)
(PR1a-F:    5'---AATATCCCACTCTTGCCG-3', (SEQ ID NO: 4)
PR1a-R:     5'-CCTGGAGGATCATAGTTG-3', (SEQ ID NO: 5)
PR1b-F:     5'-ATCTCACTCTTCTCATGC-3', (SEQ ID NO: 6)
PR1b-R:     5'-TACCTGGAGGATCATAGT-3', (SEQ ID NO: 7)
PR1c-F:     5'-CTTGTCTCTACGCTTCTC-3', (SEQ ID NO: 8)
PR1c-R:     5'-AACACGAACCGAGTTACG-3', (SEQ ID NO: 9)
PR1-F:      5'-TTCACAACCAGGCACGAGGAG-3', (SEQ ID NO: 10)
PR1-R:      5'-CCAGACAAGTCACCGCTACCCCAGGCTAA-3', (SEQ ID NO: 11)
PDF1.2-F:   5'-TCACCCTTATCTTCGCTGCTC-3', (SEQ ID NO: 12)
PDF1.2-R:   5'-GTTGCATGATCCATGTTTGG-3', (SEQ ID NO: 13)
ERF1-F:     5'-TCAGAAGACCCCAAAAGCTC-3', (SEQ ID NO: 14)
ERF1-R:     5'-TTGATCACCGCTCCGTGAAG-3'.
```

At Hour 0, Hour 3, and Hour 6 after inoculating tobacco with the pathogen, the tobacco leaves were added to liquid nitrogen for storage, and then used for RNA isolation. After grinding the tobacco leaves using a mortar and pestle and liquid nitrogen, RNA was extracted from tobacco leaves by using the TRIzol reagent (Invitrogen Life Technologies). The extracted RNA was used for the RT reaction using M-MLV RT enzyme (Enzynomics). Then, qRT-PCR was performed using cDNA obtained from the RT reaction. Conditions for qRT-PCR included initial denaturation for 10 minutes at 95° C., DNA synthesis and detection with 40 cycles (30 seconds at 95° C.; 60 seconds at 55° C.; and 30 seconds at 72° C.), and elongation for 1 minute at 72° C. as a final step.

Example 1

Results of the In Vitro Analysis of ISR

The metagenome was obtained from Micro Bank and its metagenome pool is shown in FIG. 1.

Figure 2:
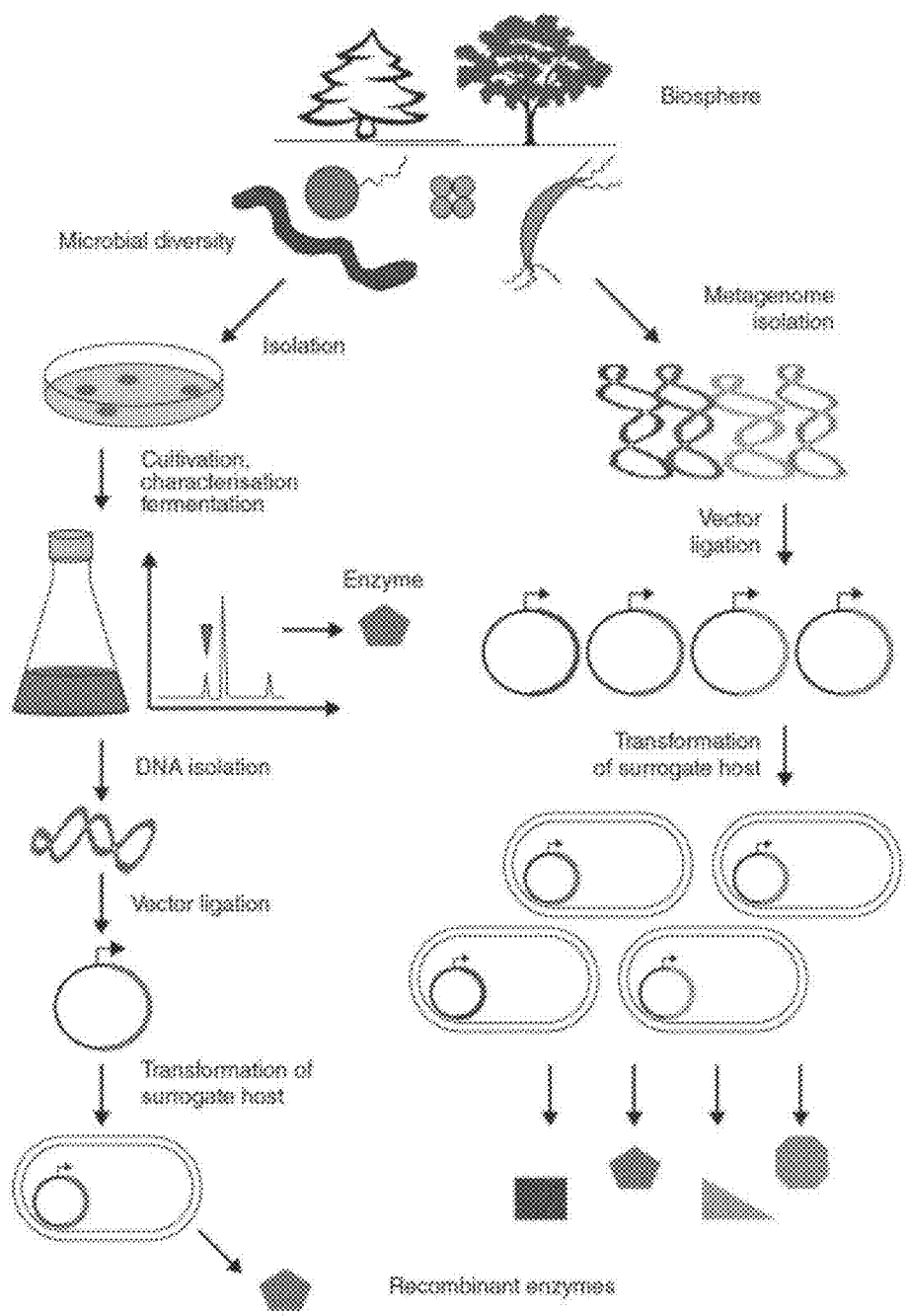
FIG. 2 illustrates a method for constructing a soil metagenome in *E. coli*. The DNA fragment was inserted into a fosmid vector (pCCIFOS) and then was transformed into *E. coli* (EPI300).

The metagenome was obtained in a state wherein each metagenome isolated from the soil was inserted into a fosmid (pCCIFOS) vector and transformed in *E. coli* (FIG. 2).

Figure 3A:
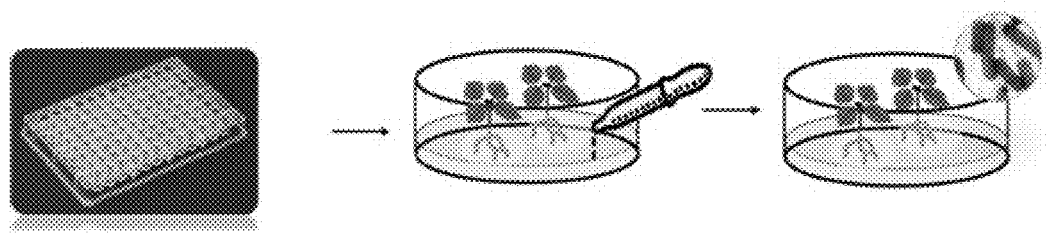
FIG. 3A illustrates process of applying the soil metagenome pool to tobacco roots after culturing the metagenome library.
Figure 3B:
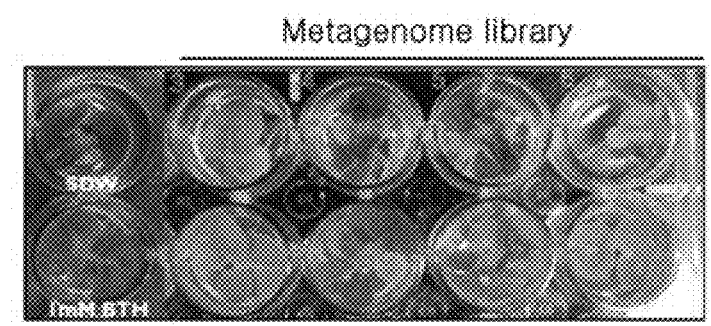
FIG. 3B shows the results obtained by observing symptoms of disease 1-2 days after inoculating the pathogen to tobacco leaves. The positive control group plant was treated with 1 mM benzothiadiazole (BTH) as a chemical trigger for eliciting induced resistance.

The soil metagenome pool was cultured on an LB medium and applied to tobacco roots. After seven days, the tobacco leaves were inoculated with the pathogen and any symptoms of disease were monitored. The positive control group plant was treated with 1 mM BTH (FIG. 3B).

The process for obtaining a monoclone from the soil metagenome library pool started from the determination of induced resistance in 605 pools. The experiment for isolating colonies from the selected pool and determining the induced resistance was performed. After selecting two monoclones, the determination was made to see which region of the gene inserted into the plasmid was responsible for expressing the induced resistance. From the 605 metagenome pool, two monoclones of 1B8-4-D7 and 1F4-2-F7 were selected (FIG. 4). The induced resistance was determined based on the method shown in FIG. 3A. With the genome obtained by cloning, following the random shearing of the subject gene in each clone by using a shotgun method, the induced resistance was determined again, and attempts to see which gene at which site expressed the induced resistance were preformed (FIG. 5A). To do so, a transposon was inserted into the selected gene site to artificially clone a mutant gene, and then the experiment for the induced resistance was carried out (FIG. 5B), then it became possible to find a corresponding gene sequence compared to the gene site of the clone obtained from the shotgun method.

For in vitro examination of the influence of the metagenome on expression of tobacco resistance gene, symptoms of the disease were observed two days after inoculation with the pathogen (FIGS. 6A-6C). The positive control group and negative control group were treated with 1 mM BTH and sterilized distilled water, respectively. As shown in FIGS. 6A-6C, both clones of 1B8-4-D7 and 1F4-2-F7 exhibited induced resistance compared to the positive control group. As a result of the transposon mutagenesis, it was found that the induced resistance observed from the shotgun method was not exhibited. Based on these results, it was found that 1B8-4-D7 gene was involved with induced resistance in plants.

Example 2

Expression Analysis of the Resistance Gene

For in vitro determination of the influence of the metagenome on expression of the resistance gene in tobacco, at Hour 0, Hour 3, and Hour 6 after inoculating tobacco with the pathogen, the tobacco leaves were collected and added to liquid nitrogen for storage, and then used for RNA isolation. After grinding the tobacco leaves using a mortar and pestle and liquid nitrogen, RNA was extracted from the tobacco leaves by using the TRIzol reagent (Invitrogen Life Technologies). Then, the expression of PR1a, PR1b, and PR1c genes that are related to disease resistance in tobacco was determined based on qRT-PCR. It was found that there was no effect on the expression of PR1, PDF1.2, and ERF1, which are the resistance gene of *Arabidopsis thaliana* (FIG. 7B).

Example 3

Analysis of Induced Resistance by Selected Metagenome Clones Against *Erwinia Carotovora* Subsp. *Carotovora* as Soft-Rot Pathogen In order to see induced resistance by selected metagenome clones against *Erwinia carotovora* subsp. *carotovora* as soft-rot pathogen, fragments of the selected metagenome clones were produced. 1B8-4-D7 clones are metagenomes containing about 4.7 kb insert and pUC19 as a backbone. The insert was digested into five types of fragments by treatment with restriction enzymes EcoRI, PstI, and BamHI. Accordingly, a PstI fragment clone, BamHI fragment clone BS, and PB clone digested with PstI and BamHI, E2052 containing about 2 kb insert as digested with EcoRI, and E1266 clones containing about 1 kb EcoRI fragment were produced (FIG. 8A).

The control group was treated with sterilized distilled water and the induced resistance control group was treated with 1 mM BTH. Each clone of BS, PS, PB, E1266, E2052, and 1B8-4-D7 and *E. coli* DH5α having pUC19 were cultured on an LB medium for 16 hours. Then, 2-week old young tobacco roots were inoculated with each of them (10 ml). One week later, tobacco leaves were inoculated with *Erwinia carotova* subsp. *carotovora* and symptoms of soft-rot were observed after 24 hours.

Among the aforementioned five clones, only the BS clone exhibited induced resistance against *Erwinia carotova* subsp. *carotovora* as a soft-rot pathogen, almost at the same level as the original metagenome 1B8-4-D7. It also exhibited the induced resistance at almost the statistically same level as 1 mM BTH (i.e., the induced resistance control group) (FIG. 8B). As a result of analyzing other fragment clones and independent gene sequences in the gene inside BS by using Blast X, it was found to encode ORF of about 2.0 kb restriction endonuclease. The BS clone was named '6D2-G5'.

Example 4

Analysis of Induced Resistance by Selected Metagenome Clones Against Pepper Canker Caused by *Xanthomoans Axonopodis* Pv. *Vesicatoria* and Viral Disease To determine induced resistance by the selected the metagenome clone against pepper canker and viral disease, the control group and the induced resistance control group were treated with sterilized water and 1 mM BTH, respectively, and *E. coli* DH5α containing each clone of 1F4-2-F7, 1B8-4-D7, and 6D2-G5 was cultured for 16 hours on an LB medium.

When there were 8 to 9 pepper leaves, the plant was transplanted into a field, and the culture liquid was applied onto the roots two times with one-week intervals (50 ml per plant). From 10 days after the division, *Xanthomonas axonopodis* pv. *vesicatoria* (i.e., pepper canker pathogen), was inoculated in an amount of $10^8$ cfu/ml infiltration with an interval of 10 days. It was confirmed that the 6D2-G5 monoclone treatment group showed weaker disease symptoms than other treatments groups (FIG. 9A).

Further, as a result of measuring an occurrence of natural disease in field, it was observed that the disease symptoms of CMV were reduced in the 1B8-4-D7, 1F4-2-F7, and 6D2-G5 treatment groups compared to the control group (FIG. 9B). By using the virus detection immunostrip test kit (Agdia, Inc.), the viral disease was caused by cucumber mosaic virus (CMV).

The invention claimed is:

1. A recombinant vector comprising: a first nucleotide sequence selected from the group consisting of SEQ ID NO: 1, a sequence comprising positions 998 to 3,574 of SEQ ID NO: 1, and a sequence comprising positions 1,523 to 3,574 of SEQ ID NO: 1; and a second nucleic acid sequence heterologous to said first nucleotide sequence.

2. A host cell transformed with the recombinant vector of claim 1.

3. The transformed host cell according to claim 2, wherein said transformed host cell is *E. coli*.

4. A method for producing a protein having the amino acid sequence of SEQ ID NO: 2, the method comprising preparing the transformed host cell of claim 2, and obtaining the protein produced by the transformed host cell.

5. The method according to claim 4, wherein the transformed host cell is *E. coli*.

6. A plant disease resistance enhancer comprising the transformed host cell of claim 2 as an effective component, wherein the plant disease resistance enhancer is against *Erwinia carotovora* subsp. *Carotovora*, *Xanthomoans axonopodis* pv. *Vesicatoria*, a cucumber mosaic virus, or a combination thereof.

7. A method of enhancing resistance against a plant pathogen selected from the group consisting of *Erwinia carotovora* subsp. *Carotovora*, *Xanthomoans axonpodis* pv. *Vesicatoria*, a cucumber mosaic virus, and a combination thereof, the method comprising treating a plant with a composition comprising the transformed host cell of claim 2, wherein said plant has increased resistance to said pathogen as compared to a control plant not treated with the composition.

8. A preparation for controlling plant disease comprising the transformed host cell of claim 2, wherein the plant disease is caused by a plant pathogen selected from the group consisting of *Erwinia carotovora* subsp. *Carotovora, Xanthomoans axonpodis* pv. *Vesicatoria*, a cucumber mosaic virus, and a combination thereof.

9. A method of enhancing resistance against a plant pathogen selected from the group consisting of *Erwinia carotovora* subsp. *Carotovora, Xanthomoans axonpodis* pv. *Vesicatoria*, a cucumber mosaic virus, and a combination thereof, the method comprising:
- preparing the transformed host cell of claim 2;
- obtaining the protein produced by the transformed host cell; and
- treating a plant with a composition comprising the protein, wherein said plant has increased resistance to said plant pathogen as compared to a control plant not treated with the composition.

* * * * *